United States Patent
Duger et al.

(10) Patent No.: US 9,901,466 B2
(45) Date of Patent: Feb. 27, 2018

(54) THREADED KNEE PROSTHESIS JOINT

(71) Applicant: ORTOTEK ORTOPEDI PROTEZ ORTEZ REHABILITASYON MERKEZI TICARET LIMITED ŞIRKETI, Ankara (TR)

(72) Inventors: Mustafa Duger, Ankara (TR); H. Murat Topcu, Ankara (TR); Can Mehmet Ali Ciftci, Ankara (TR); Akay Ozturk, Ankara (TR); Omur Deler, Ankara (TR)

(73) Assignee: ORTOTEK ORTOPEDI PROTEZ ORTEZ REHABILITASYON MERKEZI TICARET LIMITED SIRKETI, Ankara (TR)

( * ) Notice: Subject to any disclaimer, the term of this patent is extended or adjusted under 35 U.S.C. 154(b) by 0 days.

(21) Appl. No.: 15/507,750

(22) PCT Filed: Sep. 1, 2015

(86) PCT No.: PCT/TR2015/050082
§ 371 (c)(1),
(2) Date: Feb. 28, 2017

(87) PCT Pub. No.: WO2016/036336
PCT Pub. Date: Mar. 10, 2016

(65) Prior Publication Data
US 2017/0281370 A1    Oct. 5, 2017

(30) Foreign Application Priority Data

Sep. 2, 2014 (TR) .................................. 2014 10250
Sep. 9, 2014 (TR) .................................. 2014 10592

(51) Int. Cl.
*A61F 2/64* (2006.01)
*A61F 2/74* (2006.01)

(52) U.S. Cl.
CPC .......... *A61F 2/64* (2013.01); *A61F 2002/745* (2013.01); *A61F 2002/748* (2013.01)

(58) Field of Classification Search
CPC .................................. A61F 2/64; A61F 2/646
USPC ......................................................... 623/43
See application file for complete search history.

(56) References Cited

U.S. PATENT DOCUMENTS

| | | | | |
|---|---|---|---|---|
| 3,666,299 | A * | 5/1972 | Butler | A61F 2/604 188/72.7 |
| 4,595,179 | A * | 6/1986 | Glabiszewski | A61F 2/64 188/274 |
| 6,106,560 | A * | 8/2000 | Boender | A61F 2/64 623/43 |
| 6,206,933 | B1 * | 3/2001 | Shorter | A61F 2/64 623/44 |
| 2003/0187517 | A1 * | 10/2003 | Mosler | A61F 2/64 623/26 |

(Continued)

*Primary Examiner* — Bruce E Snow
(74) *Attorney, Agent, or Firm* — Gokalp Bayramoglu

(57) ABSTRACT

The invention is related to an above-knee prosthesis knee-joint mechanism that is connected with a stump which enables the above-knee amputees to walk. The invention is a threaded prosthesis knee-joint or knee-joint prosthesis which has a moving cylinder joint that enables the movement of the tibia prosthesis that is matched with the femur that is connected with the shoe having a horizontal-angle thread and threads above the femur and the shoe.

1 Claim, 5 Drawing Sheets

(56) References Cited

U.S. PATENT DOCUMENTS

2008/0255670 A1* 10/2008 Boiten .................... A61F 2/60
                                                          623/18.11
2011/0060422 A1*  3/2011 Makower ............... A61B 17/68
                                                          623/46

* cited by examiner

THREADED KNEE PROSTHESIS JOINT

CROSS REFERENCE TO RELATED APPLICATIONS

This application is the national phase entry of International Application No. PCT/TR2015/050082, filed on Sep. 1, 2015, which is based upon and claims priority to Turkish Patent Application No. 2014/10250 filed on Sep. 2, 2014, and Turkish Patent Application No. 2014/10592 filed on Sep. 9, 2014, the entire contents of which are incorporated herein by reference.

TECHNICAL FIELD

The invention is related to an above the knee prosthesis knee-joint mechanism that is connected with a stump which enables the above knee amputee patients to walk.

BACKGROUND

Amputation is the removal of a part or whole of limb of a person because of medical reasons or accidents. This operation can be performed as medical treatment because of any disease of the person, as well as in the case that a replantation operation is not implemented after an accident that a person has had. In case of amputation, the people who have not undergone replantation are called amputees. Throughout history, various prostheses which are composed of different materials have been used in order to enable these people to move by themselves without any support from someone else. The first prostheses in the history were generally composed of inflexible wooden materials and they were improved for little limbs like toes. It is thought that sticks have been used instead of the limbs which have been lost. However, different prostheses for different limbs have been improved for amputees to live in a more comfortable way.

Especially the improvement of above-knee prostheses, which enable amputee people to walk without using sticks or any other supports, constitutes one of the most important R&D fields. In the known state of the art, miscellaneous prostheses knee-joints exist according to different needs and demands of the users. Knee prosthesis compose a resistance for movement for the user in order to imitate the movements of lower leg and knee-joint, to imitate the functions of curling and opening the knee in a way similar to real movements of leg, and to have movement in a joint. In this way, the user is able to walk thanks to the prosthesis.

The knee joints which are used in above-knee joints are classified into five groups according to generating a movement resistance. These are mechanic systems, hydraulic systems, pneumatic systems, hybrid systems in which pneumatic and hydraulic systems are used at the same time, and magnetorheological systems in which magnetorheological liquids are used. Furthermore, the systems are classified into two systems as active and passive, according to the adjustment of the resistance of these systems. In mechanic systems, movement of above-knee prosthesis is controlled by the mechanic frictions of joint components. In hydraulic systems, the alteration of cross-sections of channels between two different sections, curling of artificial knee-joint movement, and resistance of opening are adjusted. Power is transmitted by using hydraulic principles in the course of movement of joint. In pneumatic systems, power is transmitted via gas. In hybrid systems, these two power transmission-mediums are used together. There are passive-controlled and microprocessor-controlled practices of these artificial knee-joints which are classified according to the transmission-mediums of power.

In the known state of the art, hydraulic, pneumatic, and hybrid joint systems take much space in order to compose the resistance against the opening of knee, and in this circumstance it will become difficult to place the entire joint into the prosthesis. These systems which are not compact prevent the user from walking properly since their gravity center of prosthesis is not compatible with one of the real knee.

A hydraulic knee joint is disclosed in U.S. Pat. No. 6,106,560A, allowing locking of the knee and damping by a piston assembly with a lever attached pivotably to a knee attachment so that the piston assembly is operated by being compressed and expanded as the distance between lower leg and the knee attachment changes. A similar knee joint is disclosed in US2003187517A1 wherein the viscosity of the damping fluid is controlled by a force field allowing electronic adjustment of the device.

In US2008255670A1, a prosthetic joint with a fluid filled compartment located at the joint is disclosed. A wall element is positioned inside the compartment and dividing it into two parts such that, it rotates together with the relative motion of prosthetic elements connected by the joint, thus changing the volumes of the compartment parts and displacing to the fluid between said parts.

Objective of the improvement of a threaded knee-joint prosthesis is to obtain a joint:
- to be adapted to all above-knee prosthesis systems easily with its compact structure;
- to have a gravity center which is located in an appropriate place for the user to move healthfully;
- to comply with the passive-controlled and microprocessor-controlled practices.

The invention is a threaded prosthesis knee-joint or knee-joint prosthesis which has a moving cylinder joint that enables the movement of tibia piece that is matched with the femur piece that is connected with a shoe having a horizontal-angle thread and threads above the femur piece and the shoe.

BRIEF DESCRIPTION OF DRAWINGS

Images and explanations are given below in order to provide a better description for a threaded knee prosthesis which has been improved by this invention.

Figure 1:
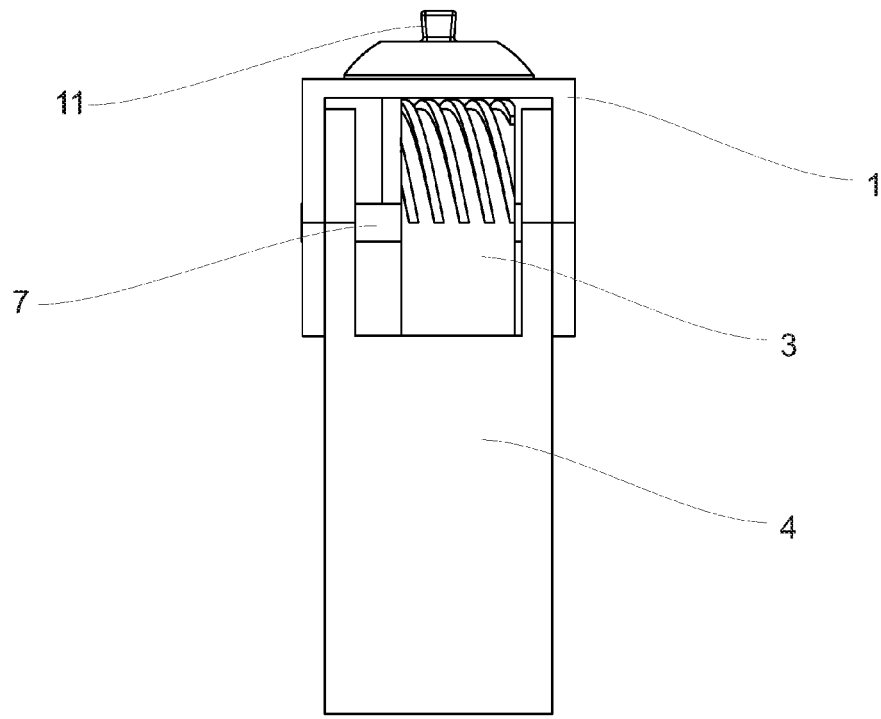
FIG. 1 Schematic front view of a threaded knee prosthesis joint.
Figure 2:
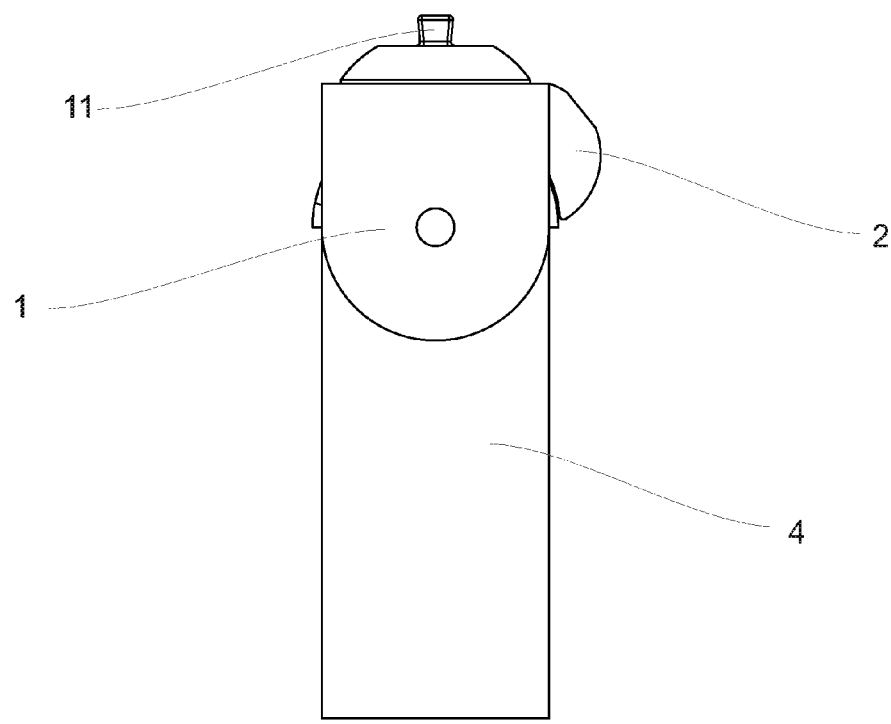
FIG. 2 Schematic side view of a threaded knee prosthesis joint at a fully open (extension) position.

In order to provide a better description for a threaded knee prosthesis joint which was improved by this invention, all pieces and parts are numbered in the figures and equivalents were given below for every single number.

1. Femur piece
2. Shoe
3. Moving cylinder
4. Tibia piece
5. Wedge
6. Groove
7. Piston shaft
8. Piston cylinder
9. Expander spring
10. Spring hanger
11. Pyramid
12. Adjuster screws
13. Receptacle cap
14. Piston ring
15. Cap of spring section
16. Ring of spring section
17. Canal
18. Valve
19. Receptacle
20. Fluid filling hole
21. Spring section
22. Spring plate

DETAILED DESCRIPTION OF THE INVENTION

A threaded knee prosthesis joint that is connected with a stump having a pyramid (11) which enables the amputees to walk without any support from someone else, basically comprise the components of:

A femur piece (1) on which the pyramid (11) is placed, that directs the movement of femur to the joint during the movement of user, which is positioned like an extension of the femur.

A shoe (2), having threads and fastened above the femur piece (1), matched with threads above the moving cylinder (3), Moving cylinder (3) which has a geometrical structure with its oval surface, which provides resistance for the tibia piece (4) by turning the linear movement of the piston cylinder (8) into circular movement during the circular movement of the piston cylinder (8) having threads that are matched with the threads above the shoe (2), A moving cylinder (3) which transforms hydraulic power into resistance for tibia piece (4) to be implemented, this hydraulic power is derived from the liquid movements in the movement cylinder (3) during the circular movements of the tibia piece (4) which is assembled in a way that it can revolve around the axis within the piston shaft (7) which has the tibia piece (4) and piston shaft (7) on both its ends that are moving in the receptacle (19).

A tibia piece (4) which can imitate the real movements of the tibia and has a groove (6) above it that can be matched with the wedge (5).

An extension spring

Figure 3:
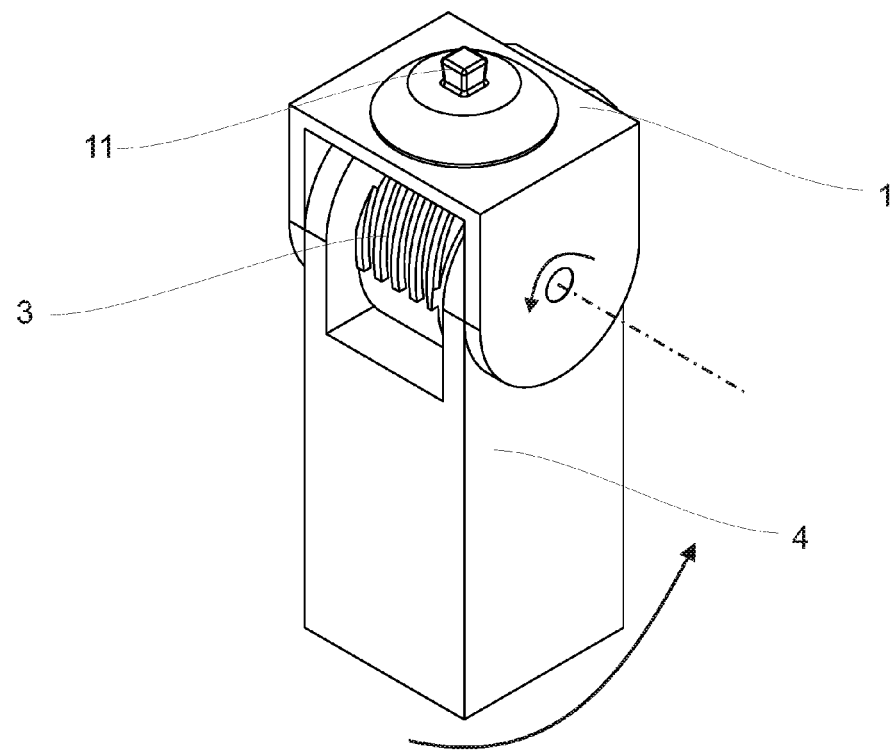
FIG. 3 Schematic isometric view of a threaded knee prosthesis joint.
Figure 4:
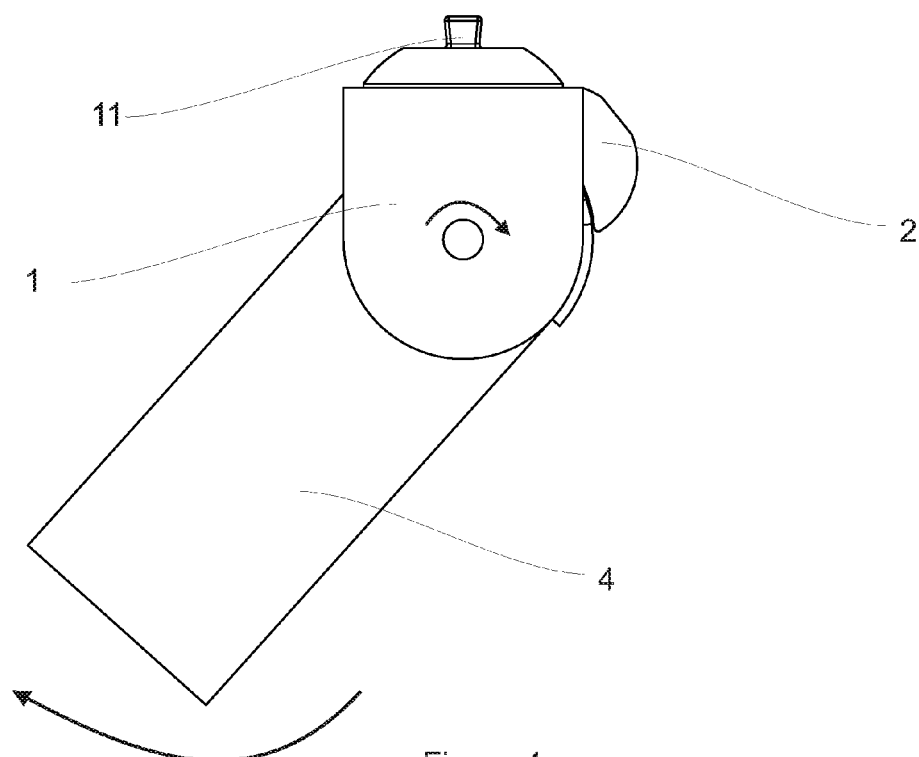
FIG. 4 Schematic side view of a threaded knee prosthesis joint at flexion position.
Figure 5:
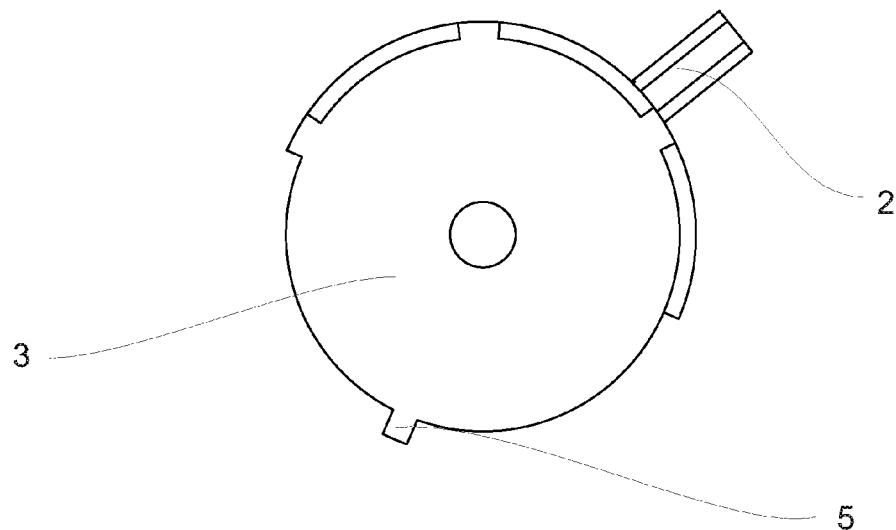
FIG. 5 Schematic side view of the moving cylinder.
Figure 6:
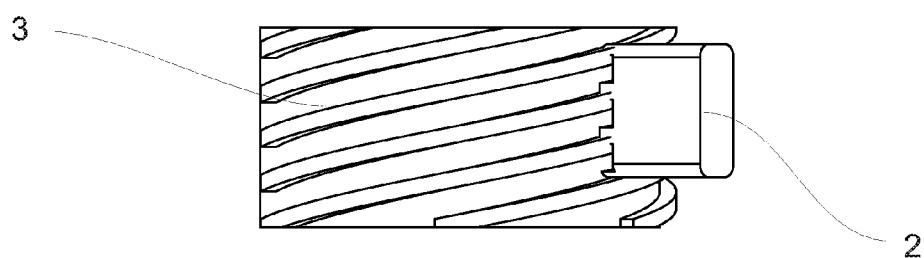
FIG. 6 Schematic top view of the moving cylinder.
Figure 7:
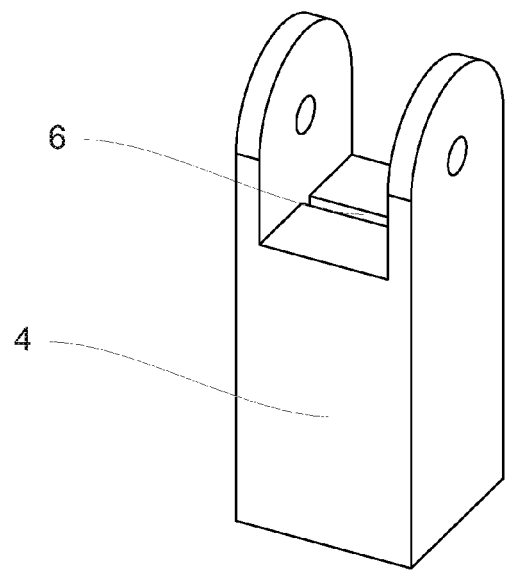
FIG. 7 Isometric view of tibia piece.
Figure 8:
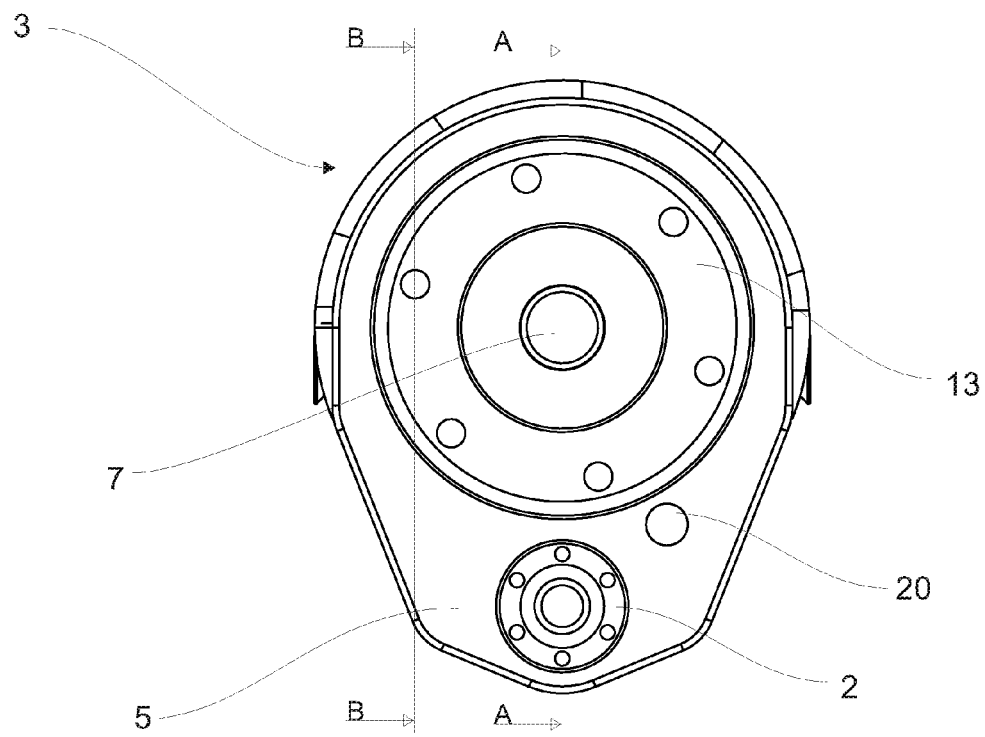
FIG. 8 Side view of the moving cylinder.
Figure 9:
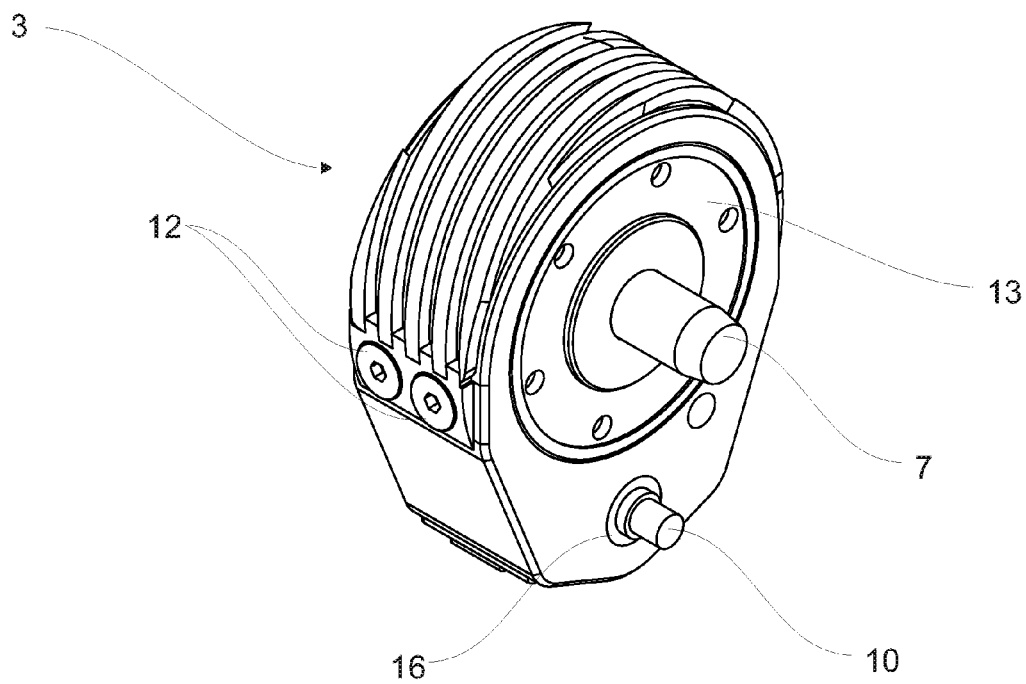
FIG. 9 Isometric view of the moving cylinder.
Figure 10:
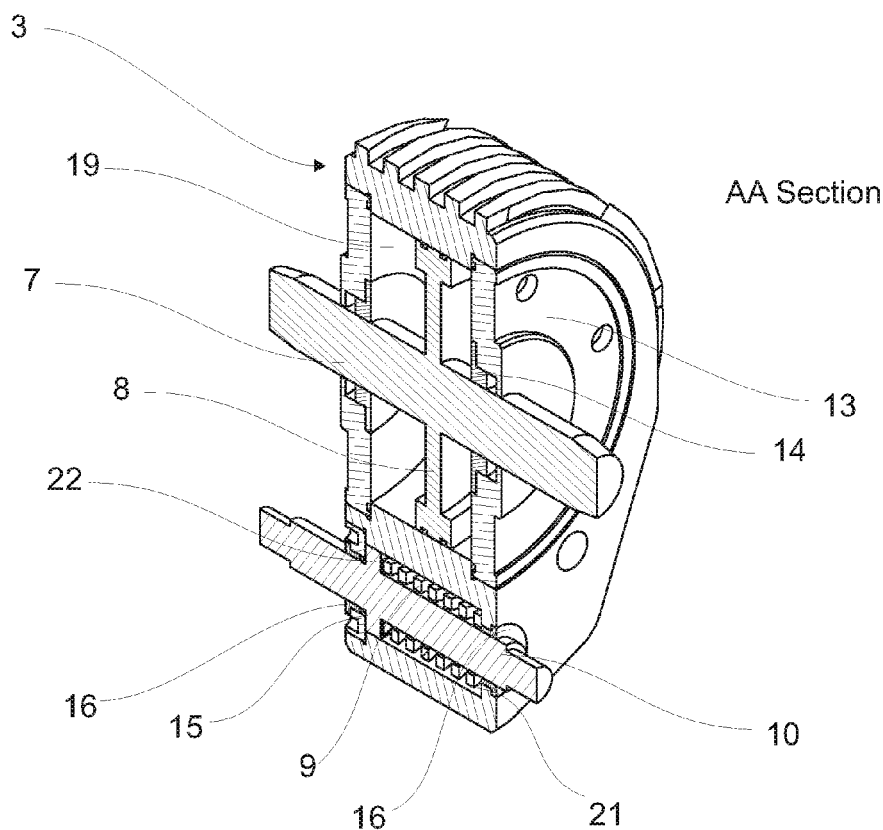
FIG. 10 A-A cross section view.
Figure 11:
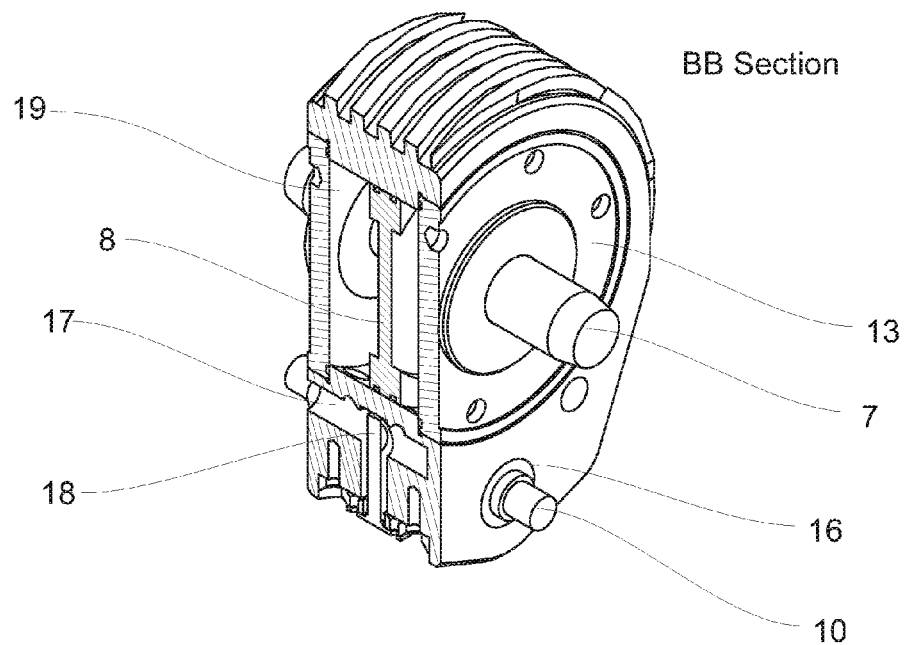
FIG. 11 B-B cross section view.

The position of the prosthesis knee joint in the position of curling the leg, is indicated in FIG. 4 schematically. The schematic view of joint prosthesis in the course of opening the leg is indicated in FIG. 3.

Femur piece (1) transmits the movement of femur into joint prosthesis which real femur (thighbone) transmits into knee joint. Femur piece (1) is connected with stump by using the pyramid (11) above it. As the user moves his/her upper leg, s/he is able to move the knee joint prosthesis which is connected with stump via pyramid (11). Shoe (2) is placed on femur piece (1) and the shoe (2) is assembled to femur piece (1) with a fixed connection element. The shoe (2) has threads on it. The screw threads and the threads on the shoe (2) are the same with the screw threads of the thread on the moving cylinder (3). Screw thread part of the shoe (2) has a concave structure.

Tibia piece (4) knee prosthesis imitates the real tibia during the movement of the user. Tibia piece (4) is connected with femur piece (1) with pin connectors. The movement of tibia piece (4) is performed around an imaginary circle between these connection pins. On the point where tibia piece (4) is connected with femur piece (1), moving cylinder (3) is connected with tibia piece (4). However, in the preferred practice of the state of the art, the movement of moving cylinder (3) is performed through the placing of wedge (5) on it, to the groove (6) on tibia piece (4). In this way, circular movements around the axis which pass through the point of connection pins of tibia piece (4) and circular movements of the moving cylinder are matched. Thus, angular speed of the moving cylinder (3) and tibia piece (4) have been equalized.

Moving cylinder (3) regulates the movement of joint prosthesis during the user's walking. While the user is walking, in course of curling and opening the leg with resistance, the support is provided for opening movement by the components of the moving cylinder (3). Inside the moving cylinder (3) is a receptacle (19) in which a fluid is incarcerated. Piston shaft (7) in a single piece and piston cylinder exists in the receptacle (19). Receptacle (19) is closed by the receptacle cap (13) which exist both two sides of the receptacle. Piston ring (14) exist within side the receptacle (19) which is above receptacle caps (13). Piston shaft (7) is passed through the homocentric holes which are above piston rings (14) and receptacle shaft (13). Piston ring (14) in which the piston shaft passes through, provides impermeability for the receptacle (19). Piston shaft (7) is assembled to tibia piece (4) irremovably. In the preferred embodiment of the invention, piston shaft (7) is also used as the pin connection of tibia piece (4) and femur piece (1). Piston cylinder (8) divides the receptacle (19) into two parts. In the points that piston cylinder (8) touches with the moving cylinder (3), segments and gaskets are used in order not to have a fluid leakage.

Since the moving cylinder (3) is matched with tibia piece (4) through groove (6) and wedge (5), it performs only linear movement relatively to tibia piece (4). In comparison with femur piece (1), the single-axis circular movement of the tibia piece (4) is able to transmit a linear movement to the moving cylinder thanks to matching of the threadeds above the convex surface of the moving cylinder and the threadeds above the shoe (2). When this movement of the moving cylinder (3) is taken into consideration, piston cylinder (8) moves in a linear way in comparison with the moving cylinder (3). The volumes of both two parts of the receptacle (19) which is divided by piston cylinder (8) are changed with this movement. With the relative movement of the piston cylinder (8), the liquids in the part decreasing volume of the receptacle (19) is directed to a liquid canal (17). In the canal (17) there is a valve (18) which adjusts the liquid flow rate. Aforementioned valve (18) is adjusted; to control liquid flow rate which is displaced by the moving cylinder (3), to control the adjuster screws (12) and to control the opening resistance of joint of the user.

Receptacle (19) which is divided by piston cylinder (8) has two exits in its both two parts into the separate canals (17). There are valves (18) which are controlled independently from each other in every single canal (17). In this way, the relative movement of piston cylinder (8) enables to circulate the liquid flow in both two ways independently from each other. In the preferred embodiment of the invention, the aforementioned valve (18) is able to change the aperture according to flow direction of the liquid. In this way, the speed of the liquid of piston cylinder (8) changes while moving into different directions, and it enables the prosthesis to have different resistances. Thus, when the user opens her/his leg and curls her/his knee while walking, the resistances provided by the prosthesis joint can be controlled separately.

After the receptacle (19) is closed, the producer fills the liquid into the receptacle (19) through filling hole (20). In addition to this, the aforementioned filling hole (20) is also used as the pathway which enables the valve to be placed. Aforementioned holes (20) are closed with sealing plugs when the liquid is filled into the receptacle (19).

In another embodiment of the invention, the pushing of tibia piece (4) while the movement of opening is provided by opening spring (9). Opening spring (9) is placed in the spring section (21) within the moving cylinder (3). Spring hanger (10) is passed through the opening spring (9) which is placed in the spring section (21). Spring plate (22) in a single piece is placed on the spring hanger (10). A spring section bushing (16) is used in order for the spring hanger (10) to be beared from both ends inside the spring housing (21). After placing the opening spring (9) and spring hanger (10) inside the spring section (21), spring chamber cap (15) is used in order to close spring section (21) and to stabilize spring hanger (10). Spring hanger (10) is matched from its two ends onto tibia piece (4). One edge of the opening spring (9) is on spring plate (22) and one edge of it is on spring chamber ring (16) which is above spring section cap (15). In this way, pushing for the necessary opening movement of the moving cylinder (3) is provided. The propulsion which is received by one surface of tibia piece (4) that is fastened with spring hanger (10), is transmitted via moving cylinder (3) and shoe (2) to the tibia piece (4) as torc and, thus, opening movement of the prosthesis is performed in an easier way. Furthermore, thanks to the precompression given by opening spring (9) which is independent from the movement of the user, the user is able to change the opening resistance depending on the user's request.

Differently from the above-mentioned embodiment of the invention which includes hydraulic liquid, a compressing spring which is placed on piston shaft (7) and whose one edge is connected with tibia piece (4) and one with femur piece (1) is also used in order for the user to control the opening resistance of joint. Thanks to this compressing spring, it will be possible to implement opening movement of the knee prosthesis in a desired speed.

Differently from the above-mentioned embodiment of the invention, torsion spring can also be used instead of compressing spring in order to control the user's resistance for opening the joint.

The invention claimed is:

1. A knee prosthesis joint for knee amputee patient, comprising:
   a femur piece acting as an extension of a femur,
   a pyramid disposed on the femur piece for connecting the femur piece to a stump of the patient,
   a tibia piece imitating a tibia,
   a shoe fixed on the femur piece,
   a moving cylinder forming a receptacle containing a fluid,
   a piston shaft running through the moving cylinder and connecting the tibia piece to the femur piece at an axis, wherein the tibia is configured to revolve around the axis,
   a piston cylinder inside the receptacle, dividing the receptacle into two parts,
   wherein the knee prosthesis joint further comprises:
   a plurality of screw threads on an oval surface of the moving cylinder and the shoe, wherein the screw threads on the oval surface of the moving cylinder and the screw threads on the shoe match with each other,
   a groove on the tibia piece, and
   a wedge fixed to the moving cylinder and slides in the groove;
   wherein an angular motion of the tibia piece around the piston shaft results in a linear motion of the moving cylinder along the piston shaft.

* * * * *